United States Patent [19]
Cadichon et al.

[11] Patent Number: 5,163,450
[45] Date of Patent: Nov. 17, 1992

[54] HARNESS FOR PREVENTING GLENO-HUMERAL JOINT SUBLUXATION

[76] Inventors: Gregory Cadichon, 1110 Lockwood Dr., Buffalo Grove, Ill. 60089; Thomas J. Loew, 728 Dodge Ave., Evanston, Ill. 60202

[21] Appl. No.: 790,814

[22] Filed: Nov. 12, 1991

[51] Int. Cl.⁵ .............................................. A61F 5/37
[52] U.S. Cl. .................................. 128/874; 128/869; 602/4
[58] Field of Search .................... 128/77, 78, 845, 846, 128/869, 874, 875, 876, 878; 602/4, 20

[56] References Cited

U.S. PATENT DOCUMENTS

| | | | |
|---|---|---|---|
| 2,358,551 | 9/1944 | Beaton | 128/77 |
| 2,980,426 | 4/1961 | Johnson | 128/77 |
| 4,497,316 | 2/1985 | Lilla | 128/77 X |
| 4,598,703 | 7/1986 | Lindemann | 128/77 X |
| 4,610,244 | 9/1986 | Hammond | 128/77 |
| 4,844,306 | 7/1989 | Ruff et al. | 128/77 X |
| 4,905,713 | 3/1990 | Morante | 128/77 X |
| 4,947,870 | 8/1990 | Larcher | 128/78 X |
| 5,020,521 | 6/1991 | Salort | 128/77 |
| 5,069,168 | 12/1991 | Roberson et al. | 128/875 X |

FOREIGN PATENT DOCUMENTS 8803013  5/1988  World Int. Prop. O. ............ 128/78

Primary Examiner—Robert A. Hafer
Assistant Examiner—Sam Rimell

[57] ABSTRACT

The harness includes a torso engaging device made of nylon strips conformed in a figure eight pattern; the arms of the wearer extending through the loops. An arm cuff is also provided which engages about the upper arm of the wearer and is connected to the torso engaging device by means of rubber tubings which act to limit range of motion of the arm. Also, to keep the torso engaging device from riding up around the arms of the wearer, further rubber tubings engage a lower torso strip section to clips engaged to the harness wearer's belt. The harness can be used for either arm, or both arms, as desired. Also, with simple modifications, the harness could be used to control range of motion of other joints as well.

12 Claims, 2 Drawing Sheets

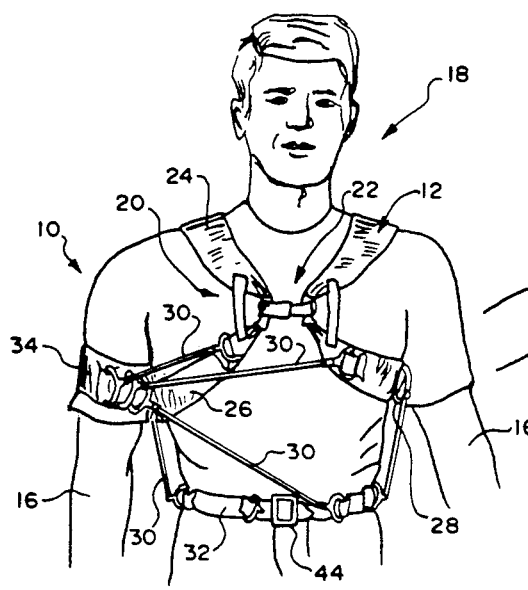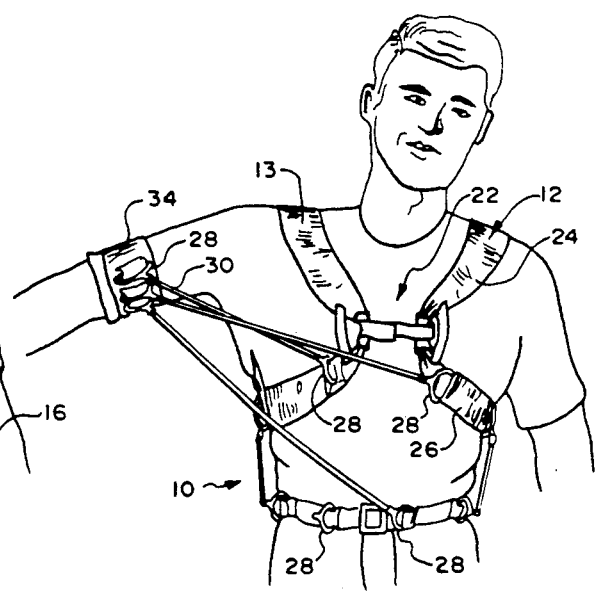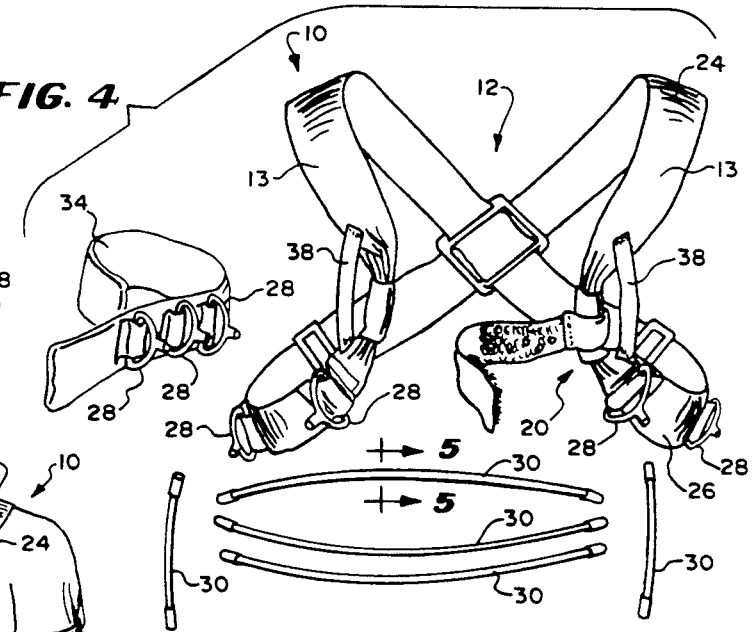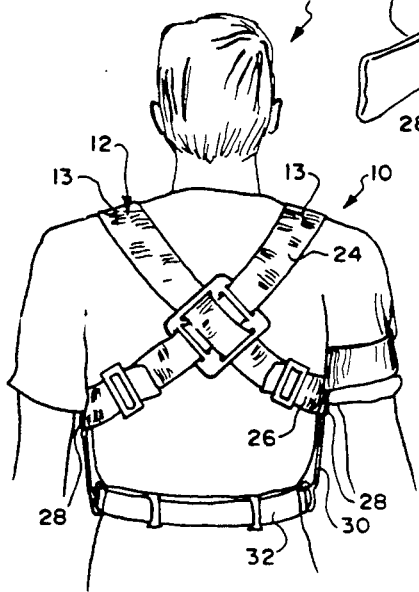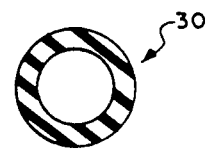

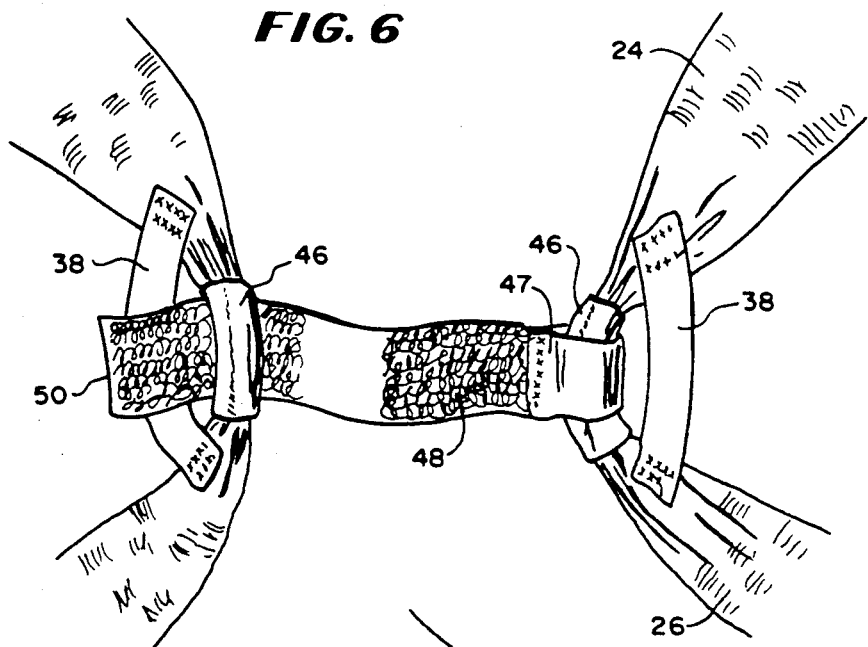
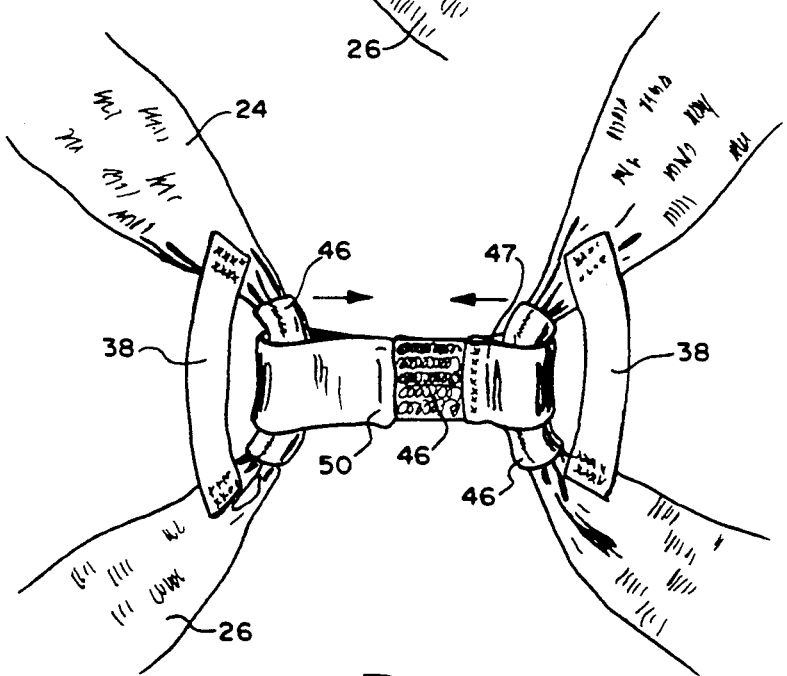
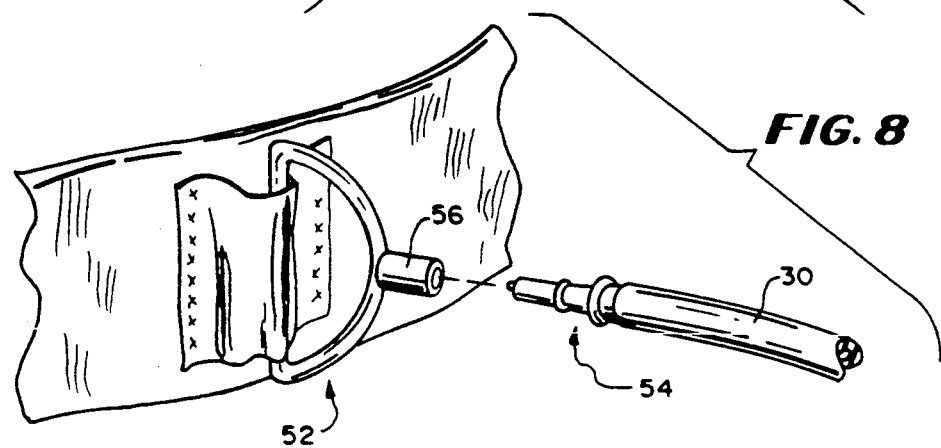

HARNESS FOR PREVENTING GLENO-HUMERAL JOINT SUBLUXATION

BACKGROUND OF THE INVENTION

The present invention pertains to a harness which engages about the upper torso of a wearer and includes structure which extends to and attaches to an appendage, such as an arm, to prevent subluxation of the joint, such as the gleno-humeral or shoulder joint. The harness is adapted to engage one or two appendages at a time.

PRIOR ART

Heretofore various devices for stabilizing a joint, such as the shoulder joint, have been proposed.

One example is disclosed in U.S. Pat. No. 4,735,198 which defines therein a body harness comprising a torso fitting portion and an appendage fitting portion secured at one end to the torso fitting portion and having the other end thereof as a free end allowing for limited mobility of the appendage to which it is fitted. At least one elastic strap extends from and is releasably secured to and between the torso fitting portion and the appendage fitting portion and controls mobility of the appendage.

Other shoulder motion restricting structures are disclosed in U.S. Pat Nos. 3,324,851; 3,970,316; 4,610,244; and 4,905,713.

These prior art restraining devices are all cumbersome, uncomfortable and cause a restriction which does not allow an athlete the freedom required in competition.

As will be described in greater detail hereinafter, the harness of the present invention is light-weight, offers a greater range of motion, and provides means for exerting a force upon an arm of the wearer which maintains the shoulder joint intact.

SUMMARY OF THE INVENTION

According to the invention there is provided a harness for limiting the range of motion of a joint, such as a gleno-humeral joint, and comprises a torso engaging device made of material strips, a cuff of material sized and configured to engage a limb adjacent the torso of the wearer, and a plurality of rubber tubings which extend between and engage to the torso engaging device and the cuff for providing increased tensioning to the cuff as the limb is abducted away from the torso. To assure that the harness does not ride up about the shoulders, it may be engaged to a belt of the wearer by further rubber tubings.

BRIEF DESCRIPTION OF THE DRAWINGS

FIG. 1 is a front view of the harness of the present invention shown on the torso of a wearer thereof.

FIG. 2 is similar to FIG. 1 but shows an arm of the wearer to which the harness is engaged abducted from the body.

FIG. 3 is a back view of the harness on the body of a wearer.

FIG. 4 is an exploded perspective view of the structures forming the harness.

FIG. 5 is a cross sectional view through one of the rubber tubings of the harness and is taken along line 5—5 of FIG. 4.

FIG. 6 is an enlarged perspective view of the closure mechanism of the harness.

FIG. 7 is similar to FIG. 5 but shows the closure mechanism in its closed state.

FIG. 8 is an enlarged perspective view of the clip members used to securing the tubings to the harness.

DESCRIPTION OF THE PREFERRED EMBODIMENT

Referring now to the drawings in greater detail, there is illustrated therein the harness of the present invention generally identified by reference numeral 10.

The harness 10 includes a shoulder straddling torso engaging device 12 which comprises a figure eight structure made of fairly wide strips 13 of nylon material. Each arm 16 of a wearer 18 fits through a loop 20 of the figure eight, with the loops 20 being releasably engaged to one another along a front center line 22 of the wearer's chest.

When viewing the harness 10 from the rear, the strips 13 cross over one another, forming an X, and can be slidably secured together in any known manner.

This slidability is necessary because the length of each strip 13 is adjustable to provide a secure yet comfortable fit for the wearer 18, the adjustability in length also being provided in any suitable fashion.

In this respect, one need merely shorten or lengthen the strips 13 to fit about the chest of the wearer 18 making it unnecessary to have the harness 10 customized for the particular wearer 18.

It will be understood that each loop 20 has an upper portion 24 and a lower portion 26 when worn. To secure the lower portion 26 of each loop from rising up about the torso of the wearer 18, a clip 28 is provided on each lower portion 26 of the strip 13 at a position underlying the arm 16 of the wearer 18. To such clip 28 is attached one end of a short hollow rubber tubing 30 which extends downwardly therefrom and engages an identical cooperating clip 28 which engages a belt 32 of the wearer 18 in a similar location.

The harness 10 further includes a cuff member 34 which may be secured about an appendage, such as the arm 16, at a point just below the joint thereof with the torso of the wearer 18.

This cuff member 34 is also formed in a manner to be adjustable in length, to accommodate various diameter appendages.

Attached to an outside surface of this cuff member 34 are a further plurality of clips 28, preferably three in number. Each of these clips 28 engages a particular rubber tubing 30 as will be defined below.

To produce a body contour accommodating harness 10, a cross strip 38 extends between converging upper and lower strip portions 24 and 26, about the area of front engagement for the harness 10. Positioned laterally of each cross strip 38 is a further clip 28 which is fixedly mounted to each lower portion 26 of the device 12.

Further, in addition to the first two clips 28 mounted on the wearer's belt 32, a second pair of clips 28 is provided, with each clip 28 being engaged to one side of a buckle 44 of the belt 32.

To control the range of motion of the arm 16, the cuff member 34 is secured about the arm 16 and engaged to the harness 10 and to the belt 32 by means of a plurality of hollow tubings 30 which are engaged therebetween in a specific manner.

In this respect, a first tubing 30 is engaged between one of the clips 28 on the cuff member 34 and the closer of the two clips 28 on the lower strip portion 26 of the device 12.

A second tubing 30 extends from one of the remaining clips 28 on the cuff member 34 to the farther clip 28 on the device 12.

Finally, a third tubing 30 is extended from the final clip 28 on the cuff 34 member to the clip 28 adjacent the buckle 44 of the belt 32 on the opposite side of the torso.

Thus, if the cuff member 34 is placed, for instance, around the right upper arm, the third tubing 30 extends from the cuff member 34 to the clip 28 to the left of the belt buckle 44.

It will be apparent that tension applied to the cuff member 34 by the tubings 30 will increase as the arm 16 is abducted further from the torso.

The tubings, as shown in FIG. 5, are made of hollow rubber and are of the type sold under the trademark Thera-Band.

Such tubing is available in a variety of resistances, as both single length tubings and loops of tubing To allow for single engagement of the two loops 20 of the device 12 to one another, the area of each loop 20 between ends of the cross strip 38 is reinforced, such as by providing a collar 46 of material therearound. Engaged over one of the collars 46 in a permanent manner is one end 47 of a strip 48 of self-engaging material, sold under the mark Velcro.

The free end 50 of the Velcro strip 48 engages about the collar 46 on the opposite loop 20 of the device 12, tightening the device 12 securely about the wearer 18.

By the provision of the adjustable Velcro strip 48 closure, as well as the provision of strips 13 which are adjustable in length, it will be understood that the harness 10 is easily accommodated to any wearer's body, making it unnecessary to have the harness 10 custom made.

Further, although a plurality of means for engaging the rubber tubings 30 are available, in the preferred embodiment, Push Apart clips made by Cole Manufacturing of Solon, Ohio under part number 3301 are used.

This clip 28 includes a base portion 52 which may be fixed to an underlying surface in any suitable manner and a plug or pin portion 54, one end of which is received within a corresponding tower 56 on the base portion 52.

To the other end of the pin portion 54 is engaged an end of the hollow tubing 30, by engagement of the pin portion 54 within the lumen of the tubing 30.

In use, as the arm 16 is moved upwardly and laterally outwardly away from the torso, tension applied to the cuff member 34 by the tubings 30 increases, providing a dynamic resistance against full range of motion which could produce a subluxation of the shoulder joint.

However, because of the configuration of the harness 10, its bulk and weight being minimal, other motions necessarily undertaken during athletic activity, are unhampered.

Also, the wearer 18 may easily engage the harness 10 about his torso and arm 16 single handedly, requiring no outside assistance.

The harness 10 disclosed herein is sized and configured for use in eliminating potential gleno-humeral joint subluxation.

It will be understood, however, that the harness 10 could be used for limiting the range of motion of other joints as well, by simply rearranging placement of the cuff member 34 thereof and by elongating or shortening, as required, the rubber tubings 30 thereof.

As described above, the harness 10 of the present invention has a number of advantages, some of which have been described above and others of which are inherent in the invention.

Also modifications may be proposed to the harness 10 without departing from the teachings herein. For example, although not shown, it will be obvious that the harness 10 may be padded for comfort.

The harness 10 has been found to be particularly useful for assisting injured basketball players so that the players can continue to play the game under certain conditions even though the shoulder may be injured. It is also believed that the harness 10 is useful for other types of injuries in other sports such as football, skiing and the like.

Accordingly, the scope of the invention should only be limited as necessitated by the accompanying claims.

For added stabilization, with contain types of injuries, it may be necessary to attach additional ties to the harness on its backside as shown in FIG. 3 and then have the opposite end of the ties connected to the cuff member 34. It's going to add stabilization to the shoulder again preventing subluxation should the arm go forward to hyper horizontal abduction and a hyper flection forward flection.

We claim:

1. A harness for stabilizing and limiting range of motion of a gleno-humeral joint comprising:
    a torso engaging device formed of material strips which criss cross over the back of the wearer, form a figure eight means engaging areas of the strips which are adjacent over the chest of the wearer, the arms of the wearer being extendible through loops of the eight formed by the strips;
    a cuff of material sized and configured to engage an area of an upper arm of the wearer;
    a plurality of resilient hollow tubes;
    means being provided on said cuff and on said torso engaging device engaging a plurality of resilient hollow tubings therebetween;
    means engageable to a belt of the wearer which are engageable to said resilient hollow tubings which extend thereto from said cuff;
    means on said torso engaging device for adjustability of the length of each strip thereof; and
    means for engaging said torso engaging device to the wearer's belt.

2. The harness of claim 1 wherein said torso engaging device and said cuff are made of nylon.

3. The harness of claim 2 wherein said rubber tubings engage only the front of the torso engaging device.

4. The harness of claim 3 wherein front terminations of the torso engaging device are engaged to one another by closure means.

5. The harness of claim 4 wherein sections of said device strips adjacent said closure, to either side of said closure, are joined to one another by cross strips.

6. The harness of claim 5 wherein said material strips are adjustable in length.

7. The harness of claim 6 wherein said cuff is adjustable in size.

8. The harness of claim 7 wherein said hollow tubings are made of rubber.

9. The harness of claim 8 wherein said tubing engaging means comprise clips.

10. A harness for stabilizing and limiting range of motion of a gleno-humeral joint comprising:

a torso engaging device formed of material strips which criss cross over the back of the wearer, form a figure eight means engaging areas of the strips which are adjacent over the chest of the wearer, the arms of the wearer being extendible through loops of the eight formed by the strips;

a cuff of material sized and configured to engage an area of an upper arm of the wearer;

a plurality of resilient hollow tubes;

means being provided on said cuff and on said torso engaging device engaging a plurality of resilient hollow tubings therebetween;

means engageable to a belt of the wearer which are engageable to said resilient hollow tubings which extend thereto from said cuff;

means on said torso engaging device for adjustability of the length of each strip thereof; and means for engaging said torso engaging device to the wearer's belt.

11. The harness of claim 10 wherein said torso engaging device and said cuff are made of nylon.

12. The harness of claim 11 wherein said tubings are comprised of rubber.

* * * * *